May 6, 1952 W. B. MOFFET Plant Pat. 1,094
ROSE PLANT
Filed Jan. 23, 1951
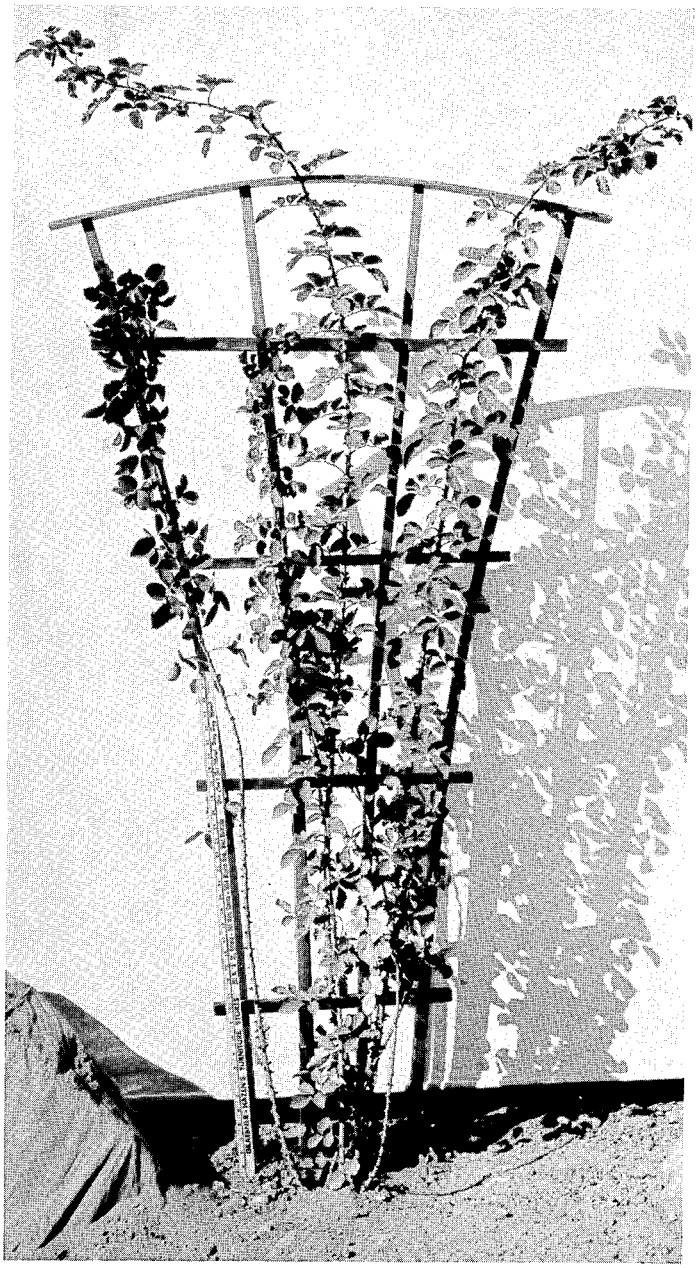
Inventor.
W. B. Moffet
By Robbs & Robbs
Attorneys.

Patented May 6, 1952

Plant Pat. 1,094

UNITED STATES PATENT OFFICE 1,094

ROSE PLANT

William B. Moffet, Gustine, Calif., assignor to Armstrong Nurseries, Inc., Ontario, Calif., a corporation of California Application January 23, 1951, Serial No. 207,277

1 Claim. (Cl. 47—61)

The present invention relates to a new and distinct variety of rose plant of the climbing hybrid tea class, originating as a bud sport of the variety "Forty-Niner" (Plant Patent No. 792), and dominantly distinguished therefrom by its climbing habit of growth. The new variety was discovered by me among the cultivated nursery rows of "Forty-Niner" plants growing on property under my direct management and control.

The parent variety is a bush rose of the hybrid tea class, and is primarily notable for its vigorous, upright growing habit, for its production of flat, glossy dark-green, medium size foliage during spring growth, with increase in size until attainment of large proportions during later summer and fall, for its resistance to disease, the attractive shape of its bud and open bloom, combined with wide contrast between the color of the outer and inner petal surfaces, as well as the extreme brilliance of the latter in the opening bud and newly opening flower. However, this bush parent, so far as I am aware, has never exhibited a climbing habit, and its growth has been that of the average strong bush rose, and usually attains a height of only 3½ to 4½ feet.

The new variety is substantially identical with its parent, except that it definitely is a climber, as evidenced by its strong canes which attain a height at maturity of 12 to 14 feet or more, and in addition, it is characterized by its habit of producing many more flowers in the spring than can usually be found at any one time on the bush variety "Forty-Niner," with an intermittent flowering habit during the remainder of the growing season.

In view of the similarities in general characteristics between the new variety and its parent, it is unnecessary to describe the new variety in detail, since, except for the aforementioned distinctions, it substantially conforms to the detailed description contained in the above-noted patent, to which reference may be readily had.

Asexual reproduction of the new variety by budding at Ontario, California, shows that the foregoing characteristics come true to form and are established and transmitted through succeeding propagations.

The accompanying drawing shows a specimen plant of the new variety in association with a marked scale having the form of a yard-stick, and illustrates the typical climbing habit of growth of the new variety.

I claim:

A new and distinct variety of rose plant of the climbing hybrid tea class, characterized by being substantially identical with its parent "Forty-Niner" (Plant Patent No. 792), but essentially distinguished therefrom by its climbing habit of growth, by its habit of producing many more flowers in the spring than can usually be found at any one time on the bush parent, and by its intermittent flowering habit during the remainder of the growing season, substantially as shown and described herein.

WILLIAM B. MOFFET.

No references cited.